US008410193B2

(12) United States Patent
Day

(10) Patent No.: US 8,410,193 B2
(45) Date of Patent: Apr. 2, 2013

(54) SILANE COATING PROCESS FOR HIGH ALKALI BIOACTIVE GLASSES

(76) Inventor: Thomas E. Day, Rolla, MO (US)

( * ) Notice: Subject to any disclaimer, the term of this patent is extended or adjusted under 35 U.S.C. 154(b) by 0 days.

(21) Appl. No.: 12/367,521

(22) Filed: Feb. 7, 2009

(65) Prior Publication Data
US 2011/0213468 A1 Sep. 1, 2011

Related U.S. Application Data

(60) Provisional application No. 61/027,025, filed on Feb. 7, 2008.

(51) Int. Cl.
A61K 6/083 (2006.01)
A61F 2/00 (2006.01)
(52) U.S. Cl. ............... 523/115; 216/44; 556/479
(58) Field of Classification Search ............ 216/44; 523/115; 556/479
See application file for complete search history.

(56) References Cited

U.S. PATENT DOCUMENTS

| 3,761,547 | A | * | 9/1973 | Grossman et al. | 264/0.5 |
|---|---|---|---|---|---|
| 4,442,240 | A | * | 4/1984 | Suh | 523/116 |
| 4,617,024 | A | * | 10/1986 | Broemer et al. | 623/10 |
| 4,673,354 | A | * | 6/1987 | Culler | 433/217.1 |
| 4,775,592 | A | * | 10/1988 | Akahane et al. | 428/406 |
| 5,332,429 | A | * | 7/1994 | Mitra et al. | 106/35 |
| 5,453,456 | A | * | 9/1995 | Mitra et al. | 523/116 |
| 5,670,258 | A | * | 9/1997 | Mitra et al. | 428/405 |
| 6,399,693 | B1 | * | 6/2002 | Brennan et al. | 524/494 |
| 7,058,243 | B2 | * | 6/2006 | Tao et al. | 385/12 |
| 2003/0133639 | A1 | * | 7/2003 | Tao et al. | 385/12 |
| 2007/0015110 | A1 | * | 1/2007 | Zhang et al. | 433/173 |

FOREIGN PATENT DOCUMENTS

| EP | 583733 A1 | * | 2/1994 |
|---|---|---|---|
| WO | WO 9221632 A2 | * | 12/1992 |
| WO | WO 02053107 A1 | * | 7/2002 |

* cited by examiner

Primary Examiner — James J Seidleck
Assistant Examiner — Peter A Salamon
(74) Attorney, Agent, or Firm — Brannon Robinson PC

(57) ABSTRACT

A method of preparing a ceramic-resin composite material for bone repair, including preparing a predetermined amount of pH controlled substantially anhydrous coupling agent by mixing a liquid silane material, alcohol and organic acid, producing particulate bioactive glass having a desired particle size of less than about 53 mesh, measuring a desired quantity of the particulate bioactive glass into a mixing vessel, heating the mixing vessel and particulate bioactive glass to about 100 degrees Celsius, mixing the heated quantity of particulate bioactive glass and spraying a predetermined amount of substantially anhydrous coupling agent into the heated quantity of particulate bioactive glass to define an admixture, mixing the admixture for sufficient time to define a quantity of substantially evenly coated particles, heating the quantity of substantially evenly coated particles for sufficient time to evolve excess solvent therefrom, and incorporating the quantity of substantially evenly coated particles into a resinous matrix to define a bone replacement medium.

12 Claims, 2 Drawing Sheets

SILANE COATING PROCESS FOR HIGH ALKALI BIOACTIVE GLASSES

CROSS-REFERENCE TO RELATED APPLICATIONS

This application claims priority to provisional patent application Ser. No. 61/027,025, filed Feb. 7, 2008, which is incorporated herein by reference.

TECHNICAL FIELD OF THE INVENTION

The present novel technology relates generally to the field of materials science and, more particularly, to ceramic reinforced resin matrix composites.

BACKGROUND

The composite principle states that the sum of the components in a composite can extend the physical characteristics beyond that of each individual component. This principle may be applied to ceramic reinforced, resin matrix composites to exploit the mechanical properties of the ceramic filler when used to reinforce the adaptability and setting characteristics of the resin matrix. A unique aspect of this synergy relies on the transference of the mechanical strains, loads, and the like exerted on the composite, through the resin matrix and into the ceramic filler. This transference relies upon specific mechanisms whereby the filler and resin matrix are combined and bonded physically and/or chemically. The specific properties of interest of the filler may be mechanically, biologically and/or physiologically useful properties. A challenge exists in chemically bonding the typically ceramic inorganic filler with the typically resinous organic matrix. Coupling agents are typically used in this regard and have been moderately successful in bonding the inorganic filler to the organic resin matrix.

The coupling agent plays a role in the transference of properties from the filler to the matrix. The composite properties are influenced by the composition and amount of filler and largely by the degree of coupling or chemical crosslinking at the interface of the ceramic filler and the resin matrix. More specifically, the ability to prepare any ceramic filler (typically silicates) for coupling to an acrylic matrix (DUDMA, BisGMA, TEGDMA, PMMA etc.) is a function of the selected coupling agents (i.e. silanes, siloxanes). The silane coupling process traditionally involves the acid peptisation in aqueous media of the silica bonding functionality of the silane by creating an Si—O linkage that will bond to the acidified surface of the ceramic filler. The acrylic functionality of the coupling agent plays a role in terms of adherence to the ceramic filler, while maintaining the functionality of the adjacent acrylic double-bond, that upon mixture with the resin matrix will have the ability to chemically crosslink therewith.

The above mechanism is relatively straightforward and predictable when the filler is "inert" or non-reactive. However, if a filler is reactive in a manner that makes the acid peptized linkage difficult and impractical, and the reaction of the filler affects the acrylic functionality, then the coupling with a standard silane becomes problematic for particular fillers. One such group of fillers of particular utility includes those glasses that may be described as bioactive or bio-reactive. Typically, bioactive glasses react in the body through an initial ion exchange mechanism to impart bonding to surrounding bone tissue. As these glasses are inherently reactive, the physical and chemical character of the exposed surfaces tend to be in flux under the conditions surrounding the traditional silanation process, making these glass surfaces 'moving targets' for silanation. Accordingly, the incorporation of said bioactive fillers into resin matrices has been met with difficulty in achieving appropriate coupling with such reactive alkali containing fillers.

Alkali releasing fillers represent a challenge to the traditional silanation method, the effectiveness of the acrylic groups and the eventual inclusion into a composite. Alkali that has not been well coupled will lead to poor composite properties, instability from both a mechanical and chemical standpoint. Alkali can lead to premature depletion of available amine used in crosslinking, leading to a setting composite that does not set, or to the creation of peroxide free radicals that lead to the premature autopolymerization of the composite. Neither is acceptable for stable self-setting composites. Silanation of such materials is currently done by applying a sufficiently thick coat of silane material over the reactive ceramic particles such that the silane coupling agent is adhered thereto through a physical caking mechanism, and may almost be thought of as a secondary matrix in and of itself. Thus, there remains a need for a process for applying a thin and even coating of silane coupling agent to reactive ceramic filler particles prior to their incorporation into a resinous matrix. The present invention addresses this need.

SUMMARY

The present novel technology relates generally to an anhydrous method for the silane coating of reactive ceramic materials. One object of the present novel technology is to provide an improved silanation process. Related objects and advantages will be apparent from the following description.

DETAILED DESCRIPTION

Figure 1A:
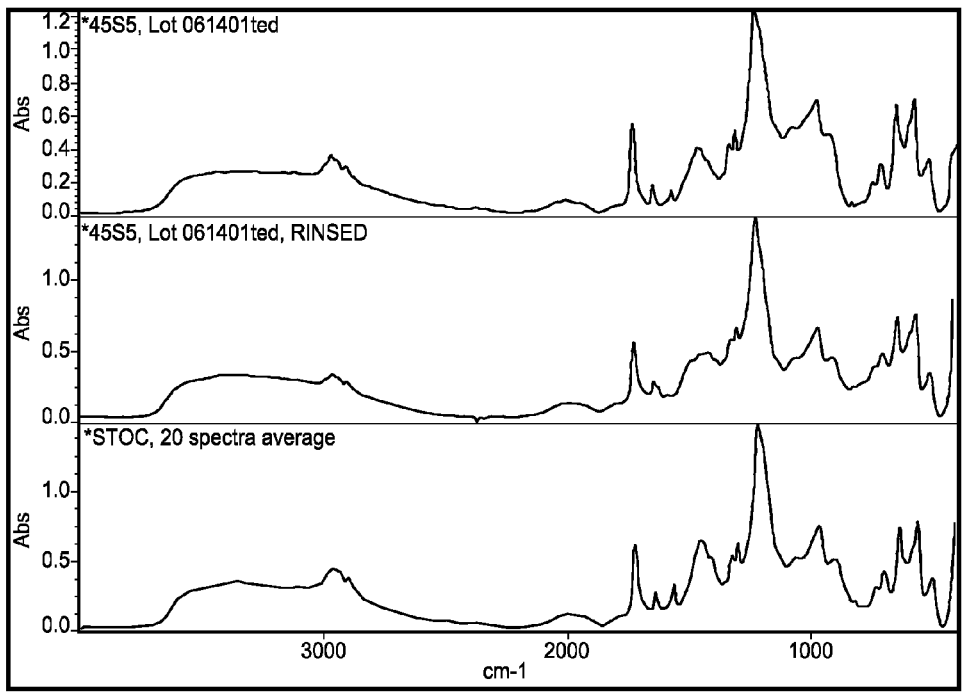
FIG. 1A is an FTIR plot of a first lot of silane coated 45S5 glass according to one embodiment of the present invention.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

The present novel technology relates to a method of coating a ceramic or like inorganic material with a substantially thin, uniform coating of silane coupling agent, such as A-174 (gamma-methacryloxypropyltrimethoxysilane), A-1100 (gamma-aminopropyltriethoxysilane), A-1120) N-beta-(aminoethyl)-gamma-aminoproipyltrimethoxysilane), A-1130 (triaminofunctional silane) and the like. While the process is particularly useful for coating reactive materials such as bioactive glass, and the specification focuses its attention and discussion on the same, it should be recognized that the present novel technology is not restricted to such materials. As presented in Table 1, common bioactive glasses include 45S5, S53P4 and 13-93 compositions. Properties of 45S5 glass include a specific gravity 2.7 g/cm$^3$, a refractive index ($n_D$) of 1.55, a softening Temp (Ts) of about 550° C., a dissolution Rate of about 150 μg/cm$^2$/day, an elastic modulus of from about 30 to about 35 Gpa, tensile strength from about 40 to about 60 Mpa, and a coefficient of thermal expansion of about 160×10$^{-7}$ cm/cm/° C.

TABLE 1 specifications of some common bioactive glasses

| | Typical compositions (wt %) | | | | | |
|---|---|---|---|---|---|---|
| | $SiO_2$ | $Na_2O$ | $K_2O$ | CaO | $P_2O_5$ | MgO | $CaF_2$ |
| 45S5 (hard/soft tissue bonding) | 45 | 24.5 | — | 24.5 | 6 | — | |
| 13-93 (hard/soft tissue bonding) | 53 | 6 | 12 | 20 | 4 | 5 | |
| 55SF (hard tissue bonding) | 52 | 19.6 | — | 11.7 | 5.8 | — | 10.9 |
| S53P4 (hard/soft tissue bonding | 53 | 23 | | 20 | 4 | | |

An alkali containing ceramic filler can impart tremendously useful biomechanical and biologic properties to a class of acrylic composites if the coupling is appropriate and successful. One embodiment of the novel technology relates to a process for producing a particulate ceramic filler material for imparting biologic behavior leading to bone bonding while maintaining the requisite composite function of load and property transfer throughout the coupled silanation of the filler in the resin matrix. It should be noted that while the examples herein focus on bioactive glass as the matrix filler material, the present novel technology may likewise be used with other filler materials, including but not limited to high alkali releasing glasses, otherwise reactive glasses, partially phase separated glasses, A/W glass, and may also be used with other ceramic, composite and structural materials.

The surface chemistry of bioactive glasses is not constant in the presence of water, as bioactive glasses, unlike most, are appreciably water soluble. Bioactive glass is substantially hydroscopic and will pick up moisture from the air, thus changing how the bioactive glass material bonds to silane groups. The ambient conditions, humidity, reaction time, and the like may be selected to effectively maintain a fresh, substantially moisture-free surface chemistry, as if the bioactive glass particles had been "just comminuted". Preparation of the glass particles to yield a substantially constant surface character may be accomplished by a variety of comminution techniques, but perhaps the most straightforward is the sequestration of the glass particles in a substantially dry environment until silane addition.

Maintenance of a constant glass particle activity while attaching the silane coupling agent allows a secure and uniform fixation of the silane coupling agent to the respective glass particles surface. This may be monitored by FTIR or other techniques showing the linkage of the coupling agent to the glass surface and the availability of the silane's C=C (double bonded carbon) in the acrylic groups.

Adapting the coupling agent for blending into the resin matrix facilitates the linkages necessary for coupling. The inorganic siloxane and the acrylic double bonds will bond to any presentable surface, but typically not reversibly. Thus, control over the extent and order of addition and exposure will dictate which bonds will crosslink and to what. Moreover, loose or lax control of these mechanisms may lead to poor coupling and matrix instability.

Example 1

Silane Solution Preparation

One consideration in the preparation of the silane solution is that substantially no water is added to hydrolytically activate the silane. A simple solution of silane (A-174) and alcohol in a ratio of 9:1 was added together and stirred, in this case with a magnetic stir plate. The pH of the solution was then adjusted to about 4.2 through the addition of acetic acid. The solution was continuously agitated and the pH was monitored and maintained at a pH of about 4.2 for one hour. The mixture was then allowed to sit under anhydrous conditions in a sealed container for at least about one hour prior to application to bioactive glass particles as a coupling agent.

Example 2

Bioactive Glass Particle Preparation

Bioactive glass particles were prepared by milling high alkaline bioactive glass to an average size of −53 microns using a VKE (Vibro Kinetic Energy) mill. A few kilograms of glass were added to the mill and allowed to mill for sufficient time to yield a quantity of appropriately-sized bioactive glass particles. The bioactive glass particles were then removed from the VKE mill and screened through a 53 micron nylon screen in a temperature and humidity controlled environment, wherein the humidity was substantially zero. In general, glass particles may range from less than 1 to greater than 1000 microns in diameter or mean cross section. The screened bioactive glass particles were then is kept dry in a sealed container (in this case, a container with PE liner) until ready for coating with silane coupling agent. When a sufficient quantity of screened bioactive glass particles had been produced and made ready for coating, the quantity of bioactive glass particles was placed in a steel mixing bowl and heated to about 100±10° C. to discourage water adsorption. The bioactive glass particles were allowed to equilibrate at the elevated temperature for at least about 2 hours prior to application of silane coupling agent.

It should be noted that the methods and processes of the present novel technology for the silanation of glass particles can be applied to other particle sizes as well as to bodies such as fibers, flakes and the like, of alternate dimensions. The novel technology arises in part from the unique challenge applying organic coatings to reactive glass and/or materials, whether due to alkali or other glass components, ceramic components, etc., that require inorganic-organic composite coupling to achieve specific, desired predictable properties.

Example 3

Coating Process

The steel bowl containing the heated bioactive glass particles of the previous example was placed on a mixer (in this case a paddle-type mixer) and using a slow speed setting was mixed using a large paddle type mixing blade. Prior to the addition of the glass particles to the mixing bowl, the surface of the bowl was coated with a non-aqueous silane-alcohol solution. While the particles were being mixed, the silane solution of Example 1 was sprayed into the particles. This spray additions process continued until all of the silane solution had been uniformly applied, being careful not to spray so heavily into any one spot as to soak the glass particles. Once the solution had been applied, mixing was continued for 15 minutes, making sure that any glass particles that became stuck or attached to the bowl were stirred back into the bulk being mixed. The glass particulate mixture was stirred for a total of 45 minutes in three 15 minute intervals. The coated filler was then spread into clean drying trays and placed in a drying oven at 50±10° C., where the glass particles were allowed to remain for seven days. The trays were kept covered to prevent airborne contamination.

Figure 1B:
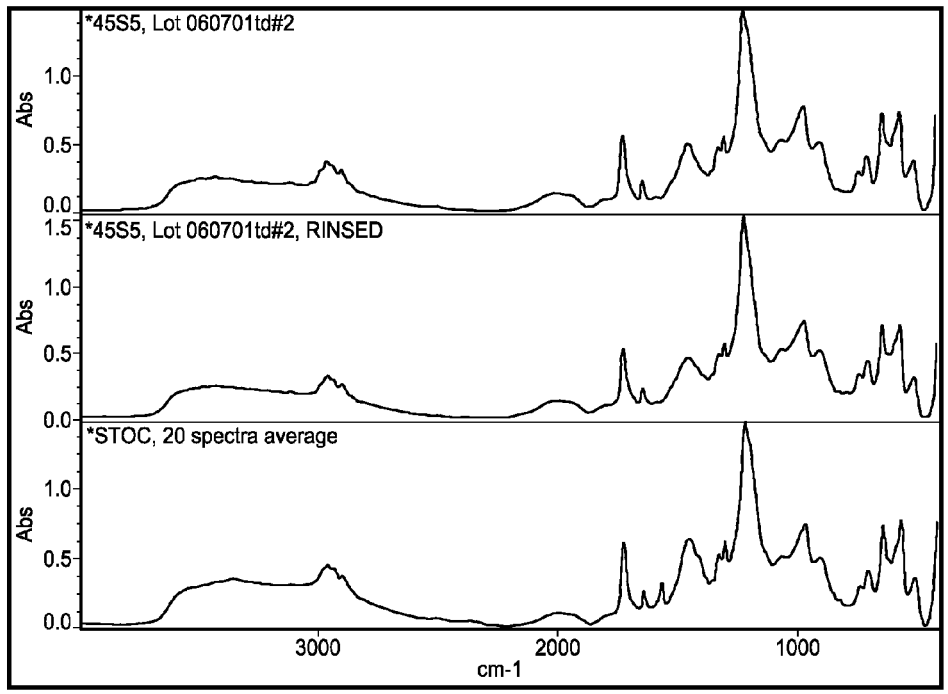
FIG. 1B is an FTIR plot of a second lot of silane coated 45S5 glass according to one embodiment of the present invention.
Figure 1C:
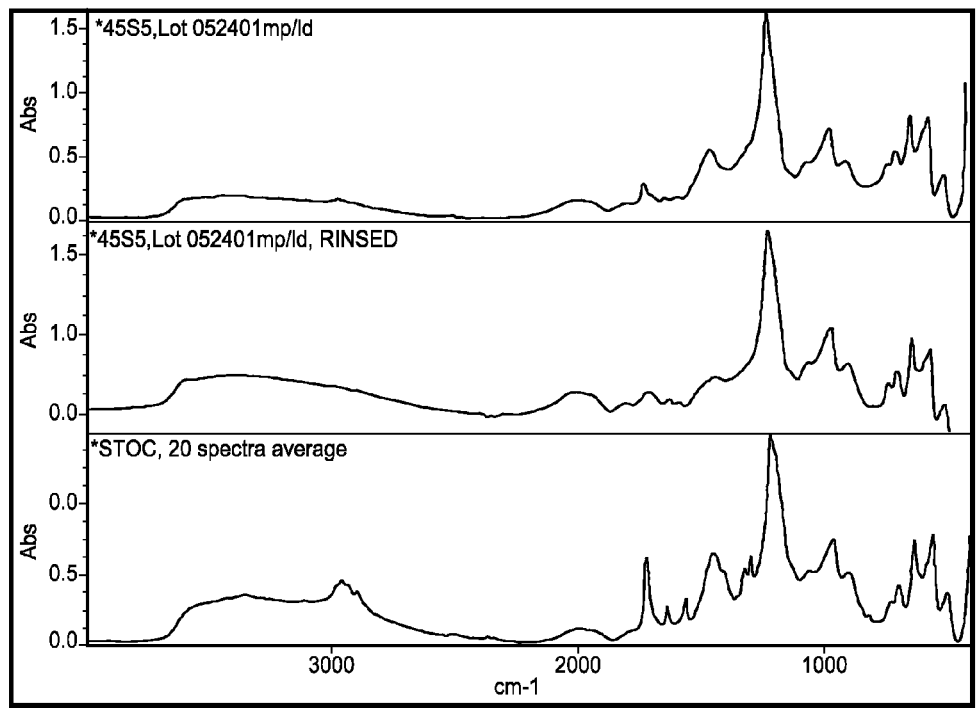
FIG. 1C is an FTIR plot of a third lot of silane coated 45S5 glass according to one embodiment of the present invention.
Figure 1D:
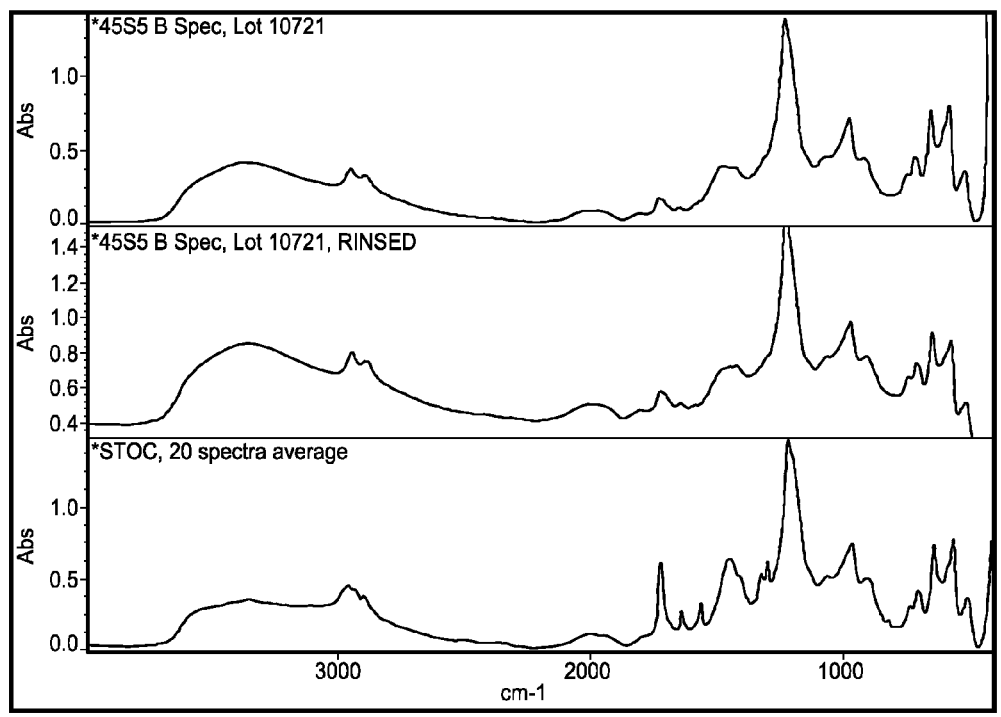
FIG. 1D is an FTIR plot of a fourth lot of silane coated 45S5 glass according to one embodiment of the present invention.

FIGS. 1A-1D show FTIR data for several 45S5 glass batches coated as described above. In each FIG., the top FTIR plot is the coated glass, the middle FTIR is the same glass after being rinsed with alcohol to remove any residual, unbounded silane, and the bottom FTIR is the standard plot for A-174 silane. The FIGs. show that after residual silane is removed, there is still a bonded coating of silane remaining on the glass particles.

The thickness of the coating is variable and depends upon the requirements of the coated particles. For example, if the coating is intended to be a protective layer keeping the high sodium content of a reactive glass from coming into direct contact with reactive components of the composite matrix (i.e., alkali-sensitive polymers, epoxies, or the like) the coating of each respective glass particle may be made relatively thick and the silane solution/coating may be present in amounts of between about 1 and about 10 weight percent, more typically between about 2 and about 8 weight percent. In contrast, if the silane coating is merely present as a bonding facilitator to promote coupling of the filler to the matrix, the coating may be much thinner, on the order of a single molecular layer. In this case, good coating uniformity may be achieved with coatings present at the 0.1 weight percent level, or even less.

The requirements of the specific application, as well as those of the end user, determine the amount of coating to be applied to the (typically) glass particles. For example, a high alkali reactive glass may require a thicker coating, so about 5 weight percent silane may be selected to provide such a coating. The weight of the glass to be coated is multiplied by the weight percent selected, here 0.05, to determine the amount of silane to be used. The silane is then weighed out. The weight of the silane is divided by about 9 to determine the amount of organic solvent required. The organic solvent is typically ethanol, but other solvents, such as methanol, acetone, or the like, may be selected. The amount of acetic (or like organic acid) to be added is 1.8 percent of the total of the silane and organic solvent. The silane, organic solvent and organic acid are combined and thoroughly mixed (typically for at least about an hour) to define a sprayable solution. The sprayable solution is then applied to the glass particles as described above, typically using a spray or misting applicator while mixing the glass particles thoroughly. This process works well for a wide range of glass batch sizes, from less than a few pounds to greater than 100 pounds.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim

1. A method of coating reactive ceramic material with an organic coupling agent, comprising:
    i) preparing a predetermined amount of pH controlled substantially anhydrous coupling agent by mixing a liquid silane material, alcohol and organic acid;
    j) producing reactive ceramic particles, the respective particles characterized by substantially unreacted surfaces;
    k) apportioning a desired quantity of the reactive ceramic particles into a mixing vessel;
    l) heating the mixing vessel and to about 100 degrees Celsius;
    m) agitating the heated quantity of reactive ceramic particles;
    n) while agitating the heated quantity of reactive ceramic particles, spraying a predetermined amount of pH controlled substantially anhydrous coupling agent into the reactive ceramic particles to define an admixture; and
    o) mixing the admixture to substantially evenly coat particles;
    wherein i) through o) occur in a substantially dry working environment.

2. The method of claim 1 and further comprising:
    p) heating the substantially evenly coated particles to remove excess solvent therefrom.

3. The method of claim 1 wherein the predetermined amount of pH controlled substantially anhydrous coupling agent is prepared by thoroughly mixing about 9 parts silane with about 1 part alcohol to define a silane-alcohol solution and adding sufficient acid to maintain a pH of about 4.2.

4. The method of claim 1 wherein the reactive ceramic particles are a high alkaline bioactive glass.

5. A method for coating reactive ceramic particles with a coupling agent, comprising:
    a) establishing a substantially dry working environment;
    b) producing reactive glass having a desired particle size;
    c) measuring a desired quantity of the particulate reactive ceramic into a mixing vessel;
    d) heating the mixing vessel and desired quantity of particulate reactive ceramic to about 100 degrees Celsius;
    e) mixing the heated quantity of particulate reactive ceramic;
    f) during e), spraying a predetermined amount of substantially anhydrous coupling agent into the heated quantity of particulate reactive ceramic to define an admixture;
    g) mixing the admixture for sufficient time to define a quantity of substantially evenly coated particles; and
    h) heating the quantity of substantially evenly coated particles for sufficient time to evolve excess solvent therefrom;
    wherein b) through h) occur in the substantially dry working environment.

6. The method of claim 5 wherein the predetermined quantity of substantially anhydrous coupling agent is prepared by thoroughly mixing about 9 parts silane with about 1 part alcohol to define a silane-alcohol solution and adding sufficient acid to maintain a pH of about 4.2.

7. The method of claim 5 wherein the reactive ceramic is a high alkaline glass having a formula of about $SiO_2$ 45% -$Na_2O$ 24.5% -$CaO$ 24.5% -$P_2O_5$ 6%.

8. The method of claim 5 wherein the anhydrous coupling agent is an anhydrous mixture of 3-(trimethoxysilyl)propyl methacrylate and alcohol.

9. The method of claim 5 wherein the substantially evenly coated particles are characterized by a coating thickness of at least one molecular layer.

10. A method of preparing a resin coated particulate ceramic, comprising:
- q) preparing a predetermined amount of pH controlled substantially anhydrous coupling agent by mixing a liquid silane material, alcohol and organic acid;
- r) producing particulate ceramic material having a desired particle size of less than about 53 mesh;
- s) measuring a desired quantity of the particulate ceramic material into a mixing vessel;
- t) heating the mixing vessel and particulate ceramic material to about 100 degrees Celsius;
- u) mixing the heated quantity of particulate ceramic material;
- v) during u), spraying a predetermined amount of substantially anhydrous coupling agent into the heated quantity of particulate ceramic material to define an admixture;
- w) mixing the admixture for sufficient time to define a quantity of substantially evenly coated particles; and
- x) heating the quantity of substantially evenly coated particles for sufficient time to evolve excess solvent therefrom;

wherein q) through x) occur in the substantially dry working environment.

11. The method of claim 10 and further comprising:
- y) incorporating the quantity of substantially evenly coated particles into a resinous matrix to define a bone replacement medium; and
- z) implanting the bone replacement medium into a human body.

12. The method of claim 10 wherein the ceramic material is a bioactive glass.

* * * * *